(12) United States Patent
Li et al.

(10) Patent No.: US 10,219,546 B2
(45) Date of Patent: Mar. 5, 2019

(54) SPRAYING ATOMIZING DEVICE

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Shuyun Hu, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 0 days.

(21) Appl. No.: 15/613,035

(22) Filed: Jun. 2, 2017

(65) Prior Publication Data

US 2017/0265526 A1    Sep. 21, 2017

(30) Foreign Application Priority Data

Jun. 3, 2016    (CN) .......................... 2016 1 0385852

(51) Int. Cl.
| | |
|---|---|
| *A24F 13/00* | (2006.01) |
| *A24F 17/00* | (2006.01) |
| *A24F 25/00* | (2006.01) |
| *A24F 47/00* | (2006.01) |
| *H05B 3/28* | (2006.01) |
| *A61M 15/06* | (2006.01) |
| *B05B 11/00* | (2006.01) |
| *H05B 3/00* | (2006.01) |

(Continued)

(52) U.S. Cl.
CPC ......... *A24F 47/008* (2013.01); *A61M 11/006* (2014.02); *A61M 11/042* (2014.02); *A61M 15/06* (2013.01); *B05B 11/00* (2013.01); *B05B 11/30* (2013.01); *H05B 3/00* (2013.01); *H05B 3/283* (2013.01); *A61M 11/007* (2014.02); *A61M 15/0021* (2014.02); *A61M 2205/3368* (2013.01); *A61M 2205/3653* (2013.01); *A61M 2205/8206* (2013.01); *H05B 2203/021* (2013.01)

(58) Field of Classification Search
CPC ...... A24F 47/008; A24F 47/00; A24F 47/002; A24F 47/006; A61M 15/06
USPC ................................................. 131/328, 329
See application file for complete search history.

(56) References Cited

U.S. PATENT DOCUMENTS

| | | | |
|---|---|---|---|
| 5,666,977 A * | 9/1997 | Higgins ................ | A24F 47/008 128/200.14 |
| 7,611,072 B2 * | 11/2009 | Peters .................. | A61M 11/041 239/13 |

(Continued)

FOREIGN PATENT DOCUMENTS

EP            0845220 A1 *    6/1998    ........... A24F 47/008

*Primary Examiner* — Abdullah Riyami
*Assistant Examiner* — Thang Nguyen
(74) *Attorney, Agent, or Firm* — Cheng-Ju Chiang

(57) ABSTRACT

An exemplary spraying atomizing device includes a housing, a liquid tank, a spraying device, a heating element, and a power supply. The housing defines an atomizing chamber. The liquid tank is configured for storing tobacco liquid. The spraying device is configured for spraying the tobacco liquid into the atomizing chamber in a form of liquid particles. The heating element is arranged in the atomizing chamber, and has a heating surface. The heating surface is configured for supporting and heating the liquid particles to form aerosol. The power supply is arranged in the housing, and is configured for feeding the heating element power.

10 Claims, 4 Drawing Sheets

(51) Int. Cl.
*A61M 11/00* (2006.01)
*A61M 11/04* (2006.01)
*A61M 15/00* (2006.01)

(56) References Cited

U.S. PATENT DOCUMENTS

| | | | |
|---|---|---|---|
| 8,820,330 B2* | 9/2014 | Bellinger | A61M 11/041 131/273 |
| 2005/0045745 A1* | 3/2005 | Kutay | B05B 7/2416 239/419 |
| 2009/0126745 A1* | 5/2009 | Hon | A24F 47/008 131/273 |
| 2009/0183744 A1* | 7/2009 | Hayton | A61M 11/007 131/270 |
| 2010/0242976 A1* | 9/2010 | Katayama | A24B 15/16 131/273 |
| 2015/0053207 A1* | 2/2015 | Knell | A61M 15/0093 128/203.12 |
| 2015/0216237 A1* | 8/2015 | Wensley | A24F 47/008 131/273 |
| 2017/0203056 A1* | 7/2017 | Dunne | B05B 11/0054 |

* cited by examiner

SPRAYING ATOMIZING DEVICE

TECHNICAL FIELD

The present invention relates to electronic cigarettes, and particularly to a spraying atomizing device.

BACKGROUND ART

An electronic cigarette includes a glass fiber core, and a heating wire in contact with the glass fiber core. The heating wire is configured for heating tobacco liquid to atomize. However, when the tobacco liquid is boiled, liquid particles of large size may be generated and inhaled by the user, rendering user unsatisfactory.

What is needed, therefore, is a spraying atomizing device, which can overcome the above shortcomings.

SUMMARY

An exemplary spraying atomizing device includes a housing, a liquid tank, a spraying device, a heating element, and a power supply. The housing defines an atomizing chamber. The liquid tank is configured for storing tobacco liquid. The spraying device is configured for spraying the tobacco liquid into the atomizing chamber in a form of liquid particles. The heating element is arranged in the atomizing chamber, and has a heating surface. The heating surface is configured for supporting and heating the liquid particles to form aerosol. The power supply is arranged in the housing, and is configured for feeding the heating element power.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
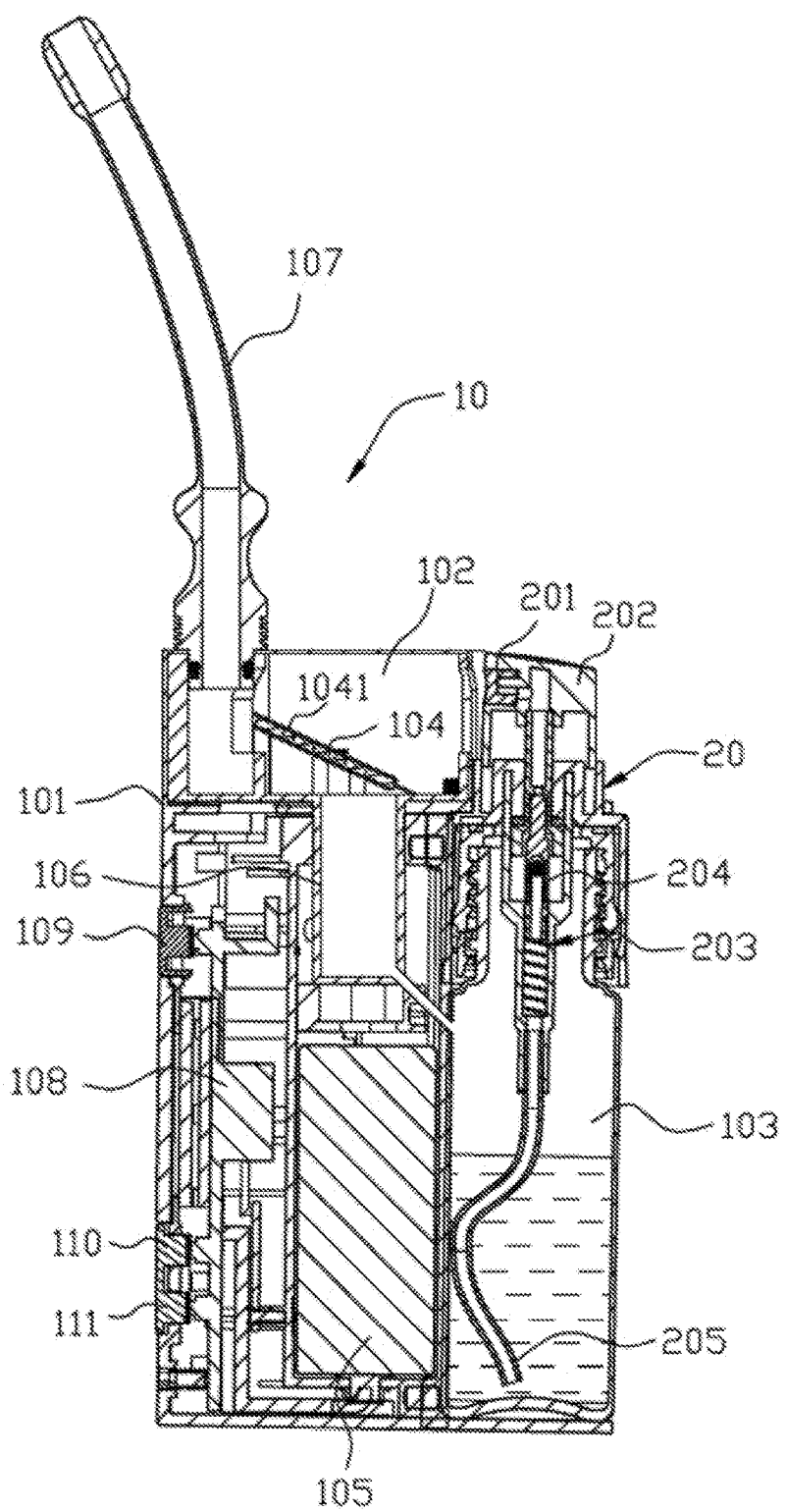
FIG. 1 is a cross-sectional view of a spraying atomizing device according to an embodiment.
Figure 2:
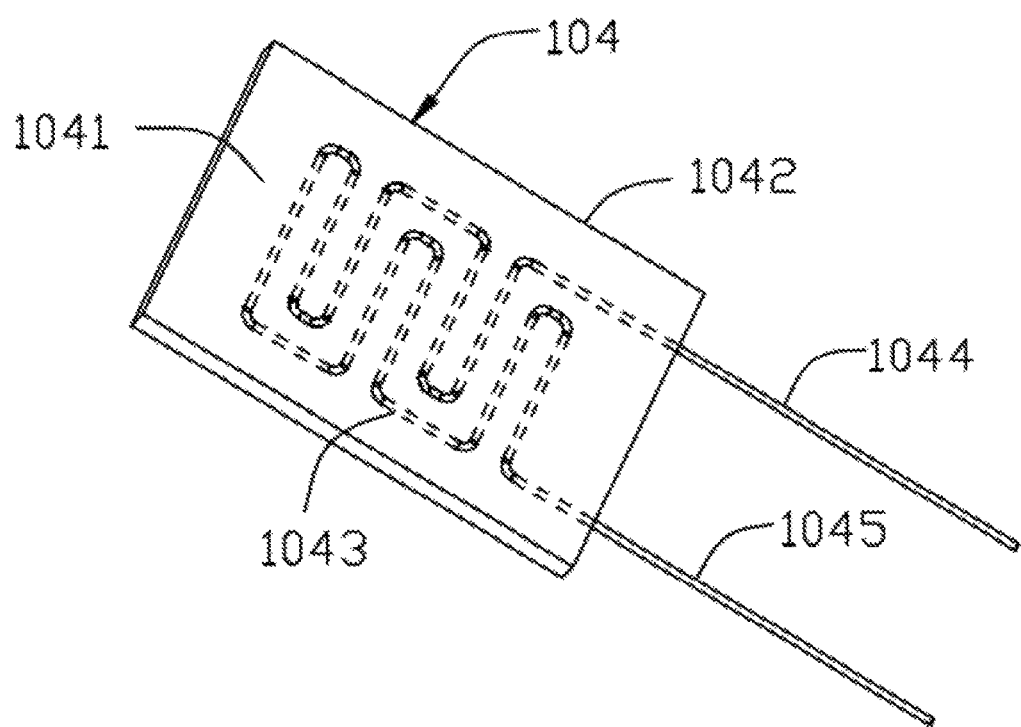
FIG. 2 is a perspective view of a heating element of the atomizing device of FIG. 1.
Figure 3:
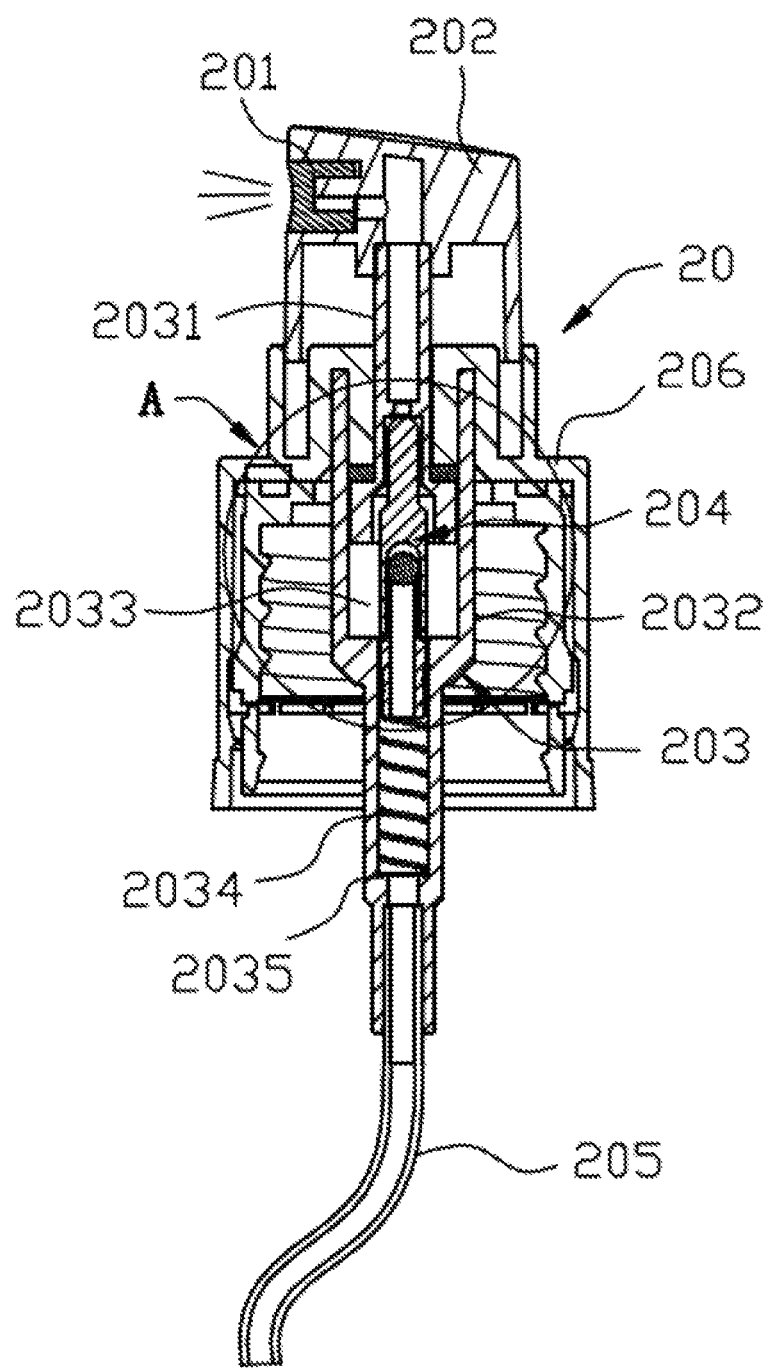
FIG. 3 is a cross-sectional view of a spraying device of the atomizing device of FIG. 1.
Figure 4:
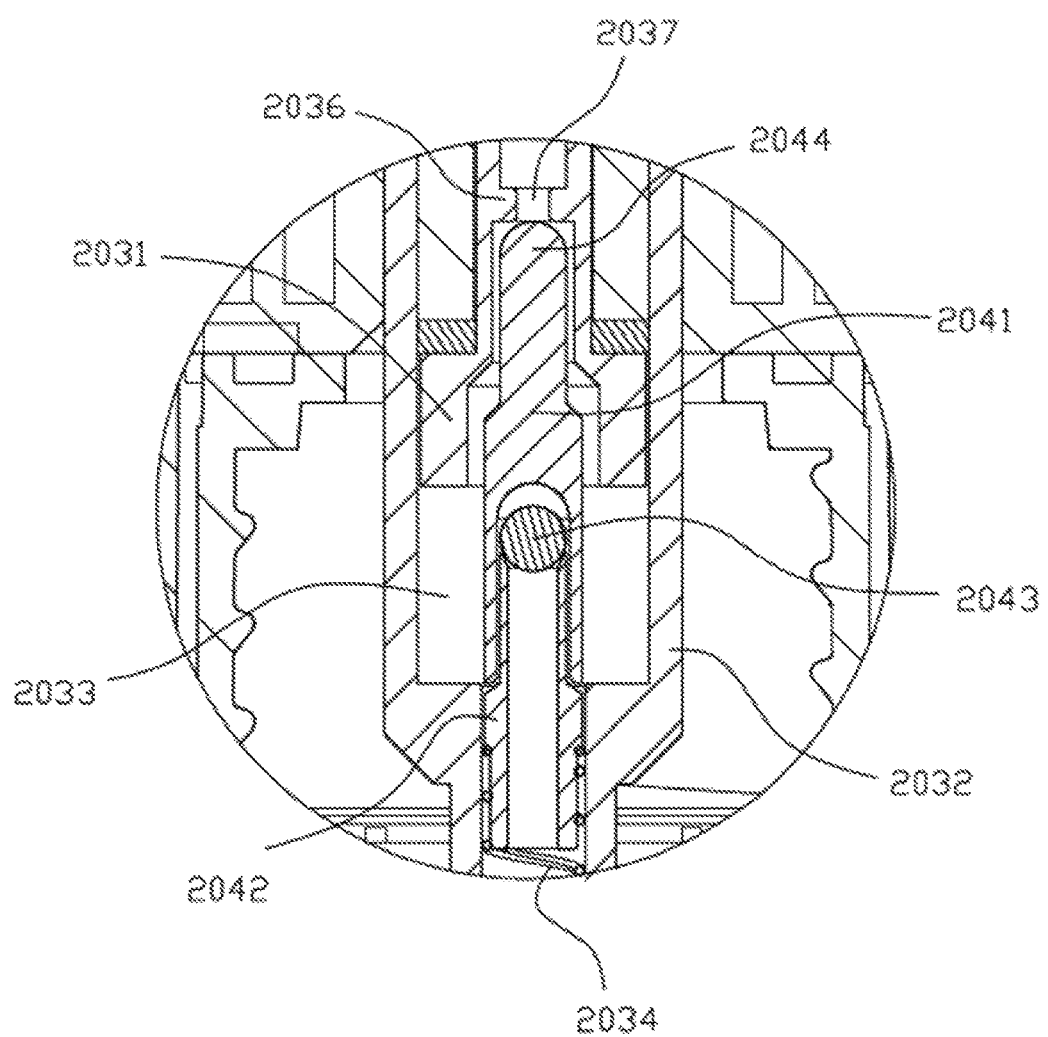
FIG. 4 is an enlarged view of area A of FIG. 3.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Referring to FIG. 1, a spraying atomizing device 10 is shown. The atomizing device 10 is configured (i.e., structured and arranged) for atomizing tobacco liquid to form aerosol. The atomizing device 10 includes a housing 101, a liquid tank 103, and a spraying device 20, a heating element 104, and a power supply 105. The spraying device 20, the heating element 104, and the power supply 105 are arranged in the housing 101.

The housing 101 defines an atomizing chamber 102 at a top part of the housing 101. The heating element 104 is arranged in the atomizing chamber 102. The spraying device 20 is configured for spraying tobacco liquid in a form of liquid particles into the atomizing chamber 102. The heating element 104 is configured for heating the liquid particles to form aerosol in a form of molecules. The spraying device 20 and the liquid tank 103 are interconnected to form an integral structure. In the present embodiment, the spraying device 20 and the liquid tank 103 may be arranged in the housing 101.

A mouthpiece 107 is provided on the housing 101. The mouthpiece 107 is in communication with the atomizing chamber 102. Quite usefully, the mouthpiece 107 and the spraying device 20 are arranged at two opposite sides of the heating element 104. The spraying device 20 sprays liquid particles into the atomizing chamber 102, the liquid particles are further atomized to aerosol in the atomizing chamber 102, and then the aerosol is expelled via the mouthpiece 107.

The liquid tank 103 is configured for storing tobacco liquid, and includes an open end. The spraying device 20 absorbs tobacco liquid from the liquid tank 103. The liquid tank 103 is connected to the spraying device 20 via the open end, for example, threadedly. When the liquid tank 103 is detached, tobacco liquid can be injected via the open end.

The power supply 105 is received in the housing 101, and is configured for supplying the heating element 104 power. The power supply 105 may be a lithium battery. The power supply 105 is electrically connected with the heating element 104 via a circuit board 108. A switch 109 is provided on the housing 101 adjacent to the circuit board 108. When the switch 109 is pressed, the heating element 104 works. Quite usefully, buttons 110, 111 are provided on the housing 101, and are configured for adjusting an output wattage of the power supply 105, e.g., increasing or decreasing the output wattage.

In the present embodiment, the heating element 104 includes a heating surface 1041. The heating surface 1041 is configured for supporting the liquid particles, and heating the liquid particles to atomize. The heating surface 1041 faces the spraying device 20, and is inclined relative to the horizontal direction. Referring to FIG. 1, in the present embodiment, an included angle between the heating surface 1041 and the horizontal direction is about 30 degrees. Accordingly, the heating element 104 can provide a large atomizing area, thus enhancing atomizing efficiency.

Quite usefully, a receiving chamber 106 is defined in the housing below the heating element 104. The receiving chamber 106 is in communication with the liquid tank 103 via a tube. Because the heating surface 1041 is inclined, liquid particles, which are not atomized, may flow into the receiving chamber 106, and then into the liquid tank 103, thus forming a circulatory system, and enhancing an atomizing efficiency. Further, liquid leakage is prevented from the atomizing chamber 102.

Referring to FIG. 2, the heating element 104 may be made of porous material, e.g., porous ceramic or porous metal. Quite usefully, the heating element 104 is made of porous ceramic. The heating element 104 includes a porous ceramic body 1042, a metallic heating part 1043, and two electrodes 1044, 1045. The heating part 1043 is embedded in the porous ceramic body 1042. Two opposite ends of the heating part 1043 are connected to the two electrodes 1044, 1045, respectively.

Referring to FIG. 3, the spraying device 20 includes a nozzle 201, a pressing head 202, a pump body 203, and a suction tube 205 connected to an end of the pump body 203. A bottom end of the suction tube 205 is immersed in the tobacco liquid. The pump body 203 is in communication with the tobacco liquid in the liquid tank 103 via the suction tube 205. An air pressure in the pump body 203 can be changed by pressing the pressing head 203, so that tobacco liquid can be sprayed via the nozzle 201 and atomized. The other end of the pump body 203 is connected to the nozzle 201. The pressing head 202 is movably arranged on the fixing holder 206. The pressing head 202 is capable of moving up and down along the fixing holder 206 to compress a space in the pump body 203, thus changing a pressure in the pump body 203. The liquid tank 103 is threadedly coupled to the fixing holder 206, and the nozzle 201 is arranged in the pressing head 202. The nozzle 201 is configured for spraying liquid particles horizontally into the atomizing chamber 102. An included angle is formed between a spraying direction of the nozzle 201 and the heating surface 1041 of the heating element 104. In this way, an area of secondary atomizing is increased. The included angle may be 30 degrees.

In the above embodiment, the atomizing device 10 includes a switch 109. In an alternative embodiment, a touch switch is provided on the housing 101 adjacent to the pressing head 202. When the pressing head 202 is pressed, the touch switch is touched simultaneously, thus activating the heating element 104.

Referring to FIGS. 3-4, the pump body 203 includes a main body 2032 and a piston 2031 arranged in the main body 2032. The piston 2031 is hollow and is in communication with the nozzle 201. A top part of the piston 2031 is connected with the pressing head 202. The pressing head 202 can push the piston 2031 to move downwards, and a sealing ring is provided between the piston 2031 and the main body 2032. A bottom part of the piston 2031 and the main body 2032 cooperatively define a compression chamber 2033. A valve body 204 is provided in the compression chamber 2033, and configured for controlling entrance of tobacco liquid into the compression chamber 2033. The main body 2032 is hollow. A bottom end of the main body 2032 is connected with the suction pipe 205. When the pressing head 202 is pressed, air or tobacco liquid in the compression chamber 2033 can be expelled via the nozzle 201 along an internal pipe of the piston 2031.

Further, the piston 2031 includes an annular stage 2036 protruding inwards. The annular stage 2036 defines a spraying hole 2037 of small diameter. A top part of the valve body 204 abuts against the annular stage 2036. A gap is defined between the annular stage 2036 and the spraying hole 2037. A spring 2034 is provided abutting against a bottom end of the valve body 204, and configured for driving the valve body 204 to restore to its initial position when the valve body 204 is moved downwards.

Quite usefully, the valve body 204 includes a top valve body 2041, a bottom valve body 2042, and a valve bead 2043. Part of the bottom valve body 2042 is nested in the top valve body 2041. The valve bead 2043 is sandwiched between the top valve body 2041 and the bottom valve body 2042. The bottom valve body 2042 is hollow and in communication with the suction tube 205. The top valve body 2041 and the bottom valve body 2042 cooperatively define a gap. The gap allows tobacco liquid to flow through. A top part 2044 of the top valve body 2041 abuts against the annular stage 2036. The top valve body 2041 and the bottom valve body 2042 are movable along an axial direction of an internal chamber of the main body 2032. A step portion 2035 is formed in the internal chamber of the main body 2032. A top end of the spring 2034 abuts against the bottom valve body 2042, and a bottom end of the spring 2034 abuts against the step portion 2035.

The working principle of the valve body 204 will be described in detail below. When the pressing head 202 is pressed, the piston 2031, the top valve body 2041 and the bottom valve body 2042 are driven to move downwards, the spring 2034 is compressed, and air in the compression chamber 2033 is compressed. The gap between the top valve body 2041 and the bottom valve body 2042 is blocked by the valve bead 2043. The air in the compression chamber 2033 cannot be expelled through the gap between the top valve body 2041 and the bottom valve body 2042, and can only be expelled via the spraying hole 2037. When the pressing head 202 is released, a negative pressure occurs in the compression chamber 2033, the spring 2034 drives the top valve body 2041, the bottom valve body 2042, and the piston 2031 to move upwards. The tobacco liquid in the liquid tank 103 flows through the suction tube 205, the internal chamber of the main body 2032, an internal chamber of the bottom valve body 2042, the gap between the top valve body 2041 and the bottom valve body 2042, and is finally sucked into the compression chamber 2033.

When the pressing head 202 is pressed again, the air in the compression chamber 2033 is compressed again, an air pressure in the compression chamber 2033 is increased, and the tobacco liquid in the compression chamber 2033 is forced to expel via a gap between the top part 2044 of the top valve body 2041 and the spraying hole 2037 in a form of fog. The tobacco liquid is finally sprayed into the atomizing chamber 102 via the nozzle 201.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. A spraying atomizing device, comprising:
a housing, the housing defining an atomizing chamber;
a liquid tank configured for storing tobacco liquid;
a spraying device configured for spraying the tobacco liquid into the atomizing chamber in a form of liquid particles;
a heating element arranged in the atomizing chamber, the heating element having a heating surface, the heating surface being configured for supporting and heating the liquid particles to form aerosol;
a power supply arranged in the housing, the power supply being configured for feeding the heating element power; and
a receiving chamber in the housing below the heating element, wherein the receiving chamber is in communication with the liquid tank, so that the liquid particles, which are not atomized, can flow into the receiving chamber.

2. The atomizing device according to claim 1, wherein the heating surface faces the spraying device, and is inclined relative to a horizontal direction.

3. The atomizing device according to claim 1, wherein the spraying device comprises a nozzle, a pressing head, a pump body, and a suction tube connected to an end of the pump body, the pump body is in communication with the tobacco liquid in the liquid tank via the suction tube, an air pressure in the pump body can be changed by pressing the pressing head, such that tobacco liquid can be sprayed and atomized via the nozzle.

4. The atomizing device according to claim 3, wherein the pump body comprises a main body, a piston in the main body, and a valve body, the piston is hollow and in communication with the nozzle, the piston and the main body cooperatively define a compression chamber, the valve body is arranged in the compression, and configured for controlling entrance of tobacco liquid into the compression chamber.

5. The atomizing device according to claim 4, wherein the pump body further comprises an annular stage and a spring, the annular stage forms a spraying hole, a top end of the valve body abuts against the annular stage, and a gap is formed between the annular stage and the spraying hole, and a bottom end of the valve body abuts against the spring.

6. The atomizing device according to claim 4, wherein the valve body comprises a top valve body, a bottom valve body, and a valve bead, part of the bottom valve being nested in the top valve body, the valve bead is sandwiched between the top valve body and the bottom valve body, the bottom valve body is hollow and in communication with the suction tube, the top valve body and the bottom valve body cooperatively define a gap.

7. The atomizing device according to claim 1, wherein the heating element is made of porous ceramic or porous metal.

8. The atomizing device according to claim 1, further comprising a mouthpiece, wherein the mouthpiece and the spraying device are arranged at two opposite sides of the heating element.

9. The atomizing device according to claim 1, further comprising a button configured for adjusting an output wattage of the power supply.

10. A spraying atomizing device, comprising:
a housing, the housing defining an atomizing chamber;
a liquid tank configured for storing tobacco liquid;
a spraying device configured for spraying the tobacco liquid into the atomizing chamber in a form of liquid particles;
a heating element arranged in the atomizing chamber, the heating element having a heating surface, the heating surface being configured for supporting and heating the liquid particles to form aerosol; and
a power supply arranged in the housing, the power supply being configured for feeding the heating element power;
wherein the spraying device comprises a nozzle, a pressing head, a pump body, and a suction tube connected to an end of the pump body, the pump body is in communication with the tobacco liquid in the liquid tank via the suction tube, an air pressure in the pump body can be changed by pressing the pressing head, such that tobacco liquid can be sprayed and atomized via the nozzle.

* * * * *